United States Patent [19]

Olson et al.

[11] Patent Number: 4,639,419

[45] Date of Patent: Jan. 27, 1987

[54] IMMUNOLOGICAL COLOR CHANGE TEST INVOLVING TWO DIFFERENTLY COLORED REAGENT SPOTS

[75] Inventors: Douglas R. Olson, Chalfont, Pa.; James R. Harness, Woodbridge; John W. Waterston, Chantilly, both of Va.

[73] Assignee: Meloy Laboratories, Inc., Springfield, Va.

[21] Appl. No.: 653,384

[22] Filed: Sep. 21, 1984

Related U.S. Application Data

[63] Continuation of Ser. No. 313,558, Oct. 22, 1981, abandoned.

[51] Int. Cl.[4] .............. G01N 33/546; G01N 33/564; G01N 33/569
[52] U.S. Cl. .......................................... 435/5; 435/7; 436/509; 436/510; 436/519; 436/523; 436/533; 436/534; 436/805; 436/808; 436/810; 436/814; 436/818; 436/828
[58] Field of Search ............... 436/509, 519, 529, 533, 436/534, 810, 805, 510, 523, 808, 814, 818, 828; 435/5, 7

[56] References Cited

U.S. PATENT DOCUMENTS 3,666,421  5/1972  Price .
3,957,436  5/1976  Murray .
4,419,453  12/1983  Dorman .

Primary Examiner—Sidney Marantz

[57] ABSTRACT

A method and device for detecting an antigenic material in which the device comprises a test utensil having an indentation in which two reagent spots are placed, the first body being a dyed substrate having a coating of an antibody or antibody-like material thereon and the second of the two reagent spots comprising a dyed test-inert material or a dyed substrate with a coating of a normal animal serum, the dye employed in the second reagent spot having a different color than that employed in the first spot. When a liquid test sample is added to the indentation, the dyed substrate particles or components are suspended or solubilized, and the resulting suspension gives the appearance of a third color. A positive agglutination test is indicated by the formation of at least one spot having the color of the first dyed substrate against a background having the color of the second dyed substrate.

46 Claims, 8 Drawing Figures

IMMUNOLOGICAL COLOR CHANGE TEST INVOLVING TWO DIFFERENTLY COLORED REAGENT SPOTS

This application is a continuation of our prior application Ser. No. 313,558, filed Oct. 22, 1981, now abandoned.

BACKGROUND OF THE INVENTION

1. Field of the Invention

The present invention is directed to a diagnostic test method and device for determining the presence of antigenic or enzmatic materials in body fluids. The instant invention relates broadly to a novel color indicating device and test method for immunological analysis of body materials and more particularly to pregnancy determination.

2. Description of the Prior Art:

A variety of physiological conditions or states, both normal and pathological, have been clinically diagnosed by a number of techniques, the more prominent being categorized as chemical, biological assay, or immunological. In many situations, the condition which is the object of the medical practitioner's determination is distinguished by the presence of one or more compounds, which because of the complexity or number of moieties present, obviates the use of chemical methods of analysis. In such instances biological assay methods, employing test animals, or immunological test procedures have been developed. It is the latter category of diagnostic means with which the present invention is concerned.

Analytical immunological or immunochemical test procedures are generally based upon an antigen-antibody reaction to determine the presence or absence of an antigen, antibody or enzyme in a body fluid ("Body fluid", as used herein, includes blood, serum, plasma, urine, cerebro-spinal fluid and saliva).

Pregnancy diagnostic tests have used both biological assay methods employing laboratory test animals and immunological test procedures. The former require the use of specific animals such as rabbits in the Friedman test or mice in the Aschheim-Zondek test. Such tests suffer from a number of disadvantages, such as, maintenance of large numbers of animals and attending facilities, particular skills in performing and analyzing the results of the tests, and the several day period required to obtain results of such tests, to name only a few.

In recent years, such biological tests have been supplanted by immunological or immunochemical tests offering many advantages. Namely, such tests may be performed in a physician's office, clinic or hospital, by technicians with less skill than that required with the biological tests. Results are usually obtained in shorter periods of time than with the older methods of diagnosis, and costs and other problems incurred in maintaining laboratory animals are avoided. In addition, immunological tests demonstrate greater specificity and sensitivity than bioassay techniques.

Most of the currently used immunological tests, particularly those employed in pregnancy determinations, fall into two broad categories, inhibition tests and direct agglutination tests. Both of these techniques, when applied to pregnancy tests, detect human chorionic gonadotropin (HCG) in the urine of pregnant women. Only in certain situations, representative of abnorml or pathological situations, is this hormonal substance encountered in non-pregnant women. The inhibition test employs erythrocyte cells or latex particles as substrate or carrier particles which are coated with HCG. A specimen of the urine being tested is initially incubated with anti-HCG. If the urine contains HCG bind to the anti-HCG present and inhibit any further binding of the antibody. An aliquot of the HCG-coated substrate particles is then added. If agglutination occurs, it indicates that the anti-HCG was free to passively agglutinate the substrate bound HCG and the conclusion is drawn that no HCG was present on the urine sample. If, however, no agglutination occurs, the inference may be drawn that HCG was present in the urine which effectively bound the anti-HCG, thus preventing interaction between the latter and the coated particles.

A direct agglutination test or latex agglutination test simply combines the specimen sample, suitably filtered and diluted with buffer solution, with a suspension of latex or other substrate particles coated with an antibody or antiserum fraction, such as anti-HCG. The presence of adequate HCG in the specimen sample will result in passive agglutination between the coated substrate particles and the HCG molecules.

Both types of tests may give inaccurate results due to false positives traceable to such things as impurities in the specimen sample and test reagents, excessive amounts of antibody coating, and too large or too small substrate particles to name but a few problems. One of the most frequent sources of error is related to the skills of the person interpreting the test. A lack of experience in interpreting test results will often lead to inaccurate results. Both categories of tests give end points which are somewhat equivocal, the latex agglutination test, for instance, indicating a positive test by a change from a milky white to a grainy white.

Many attempts have been made to develop more accurate, sensitive and definitive tests. U.S. Pat. No. 3,088,875 describes a method which incorporates a dye into a latex reagent in order to facilitate visualization of clumped or agglutinated particles. U.S. Pat. No. 3,236,732 describes a pregnancy test method in which a body fluid is combined with an antibody or antiserum of HCG and an indicator system which is broadly disclosed as an indicator material which in the presence of an antibody will agglutinate, precipitate, discolor, become colored or provide some other visible indication of the presence or absence of HCG. U.S. Pat. No. 3,862,302 discloses a single container, pregnancy diagnostic method employing stable pelletized reagents. U.S. Pat. No. 3,666,421 describes a diagnostic test slide which may be used advantageously to determine the presence of HCG in urine. The test card contains at least two dried reagent spots in close proximity which are intended to be reconstituted by addition of a liquid to be tested to form test reagents. One of the embodiments discloses the reagent spots being formed from HCG and an antiserum of HCG placed on a circle of contrasting color in order to aid in observing the test results.

Although certain advances have been made in the improvement in sensitivity, specificity, stability, and speed of immunological test procedures and the reagents and devices used therein, the techniques and materials developed heretofore have not provided a method and device which could be employed by one having little or no skill in performing such tests.

OBJECTS AND SUMMARY OF THE INVENTION

Accordingly, it is an object of the present invention to provide a test method for quickly and accrately determining the presence or absence of antigenic or enzmatic material in a body fluid which yields a color change when the specimen is positive Another object of the present invention is to provide a test method for quickly and accurately determining pregnancy based on the aforementioned color change technique.

Still another object of the present invention is to provide a test kit capable of being sold over the counter to persons without technical training for the purpose of determining pregnancy in humans.

These and other objects of the present invention will be appreciated from the description which follows.

An important advantage of the present invention resides in the provision of a color test technique for determining pregnancy and the like which is quick (i.e., on the order of 10 minutes or less), accurate, and relatively inexpensive when compared to prior techniques.

The present invention employs the direct agglutination method to detect the presence of an antigenic material in a body fluid. It should be noted that although the description which follows relates for the most part to determining pregnancy, i.e., detecting the presence of human chorionic gonadotropin (HCG) in a woman's urine as an indication of pregnancy, the instant invention should not be construed as being limited thereto. It is contemplated that the present invention has diagnostic applicability for those substances which are capable of entering into an antigen-ahtibody reaction or interaction. As used herein, "antigen or antigenic material" includes complete antigens, haptens or any proteinacious material capable of producing, stimulating production of, or reacting with antibodies. This would include but would not be limited to rheumatoid factor from persons suspected of having rheumatoid arthritis, autoantibodies from individuals suspected of having the thyroid disorder known as Hashimoto's disease; a variety of blood plasma proteins including low levels of gammaglobulin associated with such afflictions as gammaglobulinemia, pneumonia, hepatitis, pyelonephritis, septic arthritis and meningitis, fibrinogen in hypofibrinogenemia, and serum albumin; C-reactive protein in individuals suspected of having myocardial infarction, active rheumatic fever, advanced malignancy, rheumatoid arthritis, tuberculosis, pneumonia and other inflammatory diseases; blood typing generally; antigens of bacterial origin and certain drugs (for example, cocaine or morphine). Even where HCG is being tested for, the determination is not limited to detecting pregnancy but would also have applicability in testing for hydatidiform mole, choriocarcinoma or trophoblastic tumors. Nor is the present invention limited to direct agglutination since it can also be used with the well known agglutination inhibition technique. The present method and test utensil can be used with blood, serum, plasma, urine, saliva, and cerebro-spinal fluids of humans and other animals.

In accordance with the present invention a test utensil is provided having a receptacle, e.g., a well or indentation therein in which two reagent spots are adhered to the surface thereof. The first of the two reagent spots comprises a carrier or substrate material of synthetic or natural derivation, having a dye bound thereto. The dyed substrate comprises particles which are coated or sensitized with an antibody or antiserum which is the specific complement to the antigenic material which is being analyzed, the antigen and its antibody complement forming a specific antigen-antibody pair.

Within the well, and in close proximity to the first reagent spot is a second reagent spot formed from a dyed reagent. The second reagent spot may be formed from a dyed substrate such as a serum protein or inert molecule, or formed from dyed carrier particles coated in such a way that an antigen-antibody reaction does not result. The specific dyed second reagent spot cited as part of the HCG test example will be dyed particles. Both reagent spots are provided in a dry condition.

The dye employed in coloring the carrier particles of the second reagent, however, absorbs in a different part of the spectrum and, thus, is easily distinguishable from the color of the first spot by the normal human eye. (By "normal human eye" is meant vision which is not impaired by what is commonly referred to as color-blindness, in any of its manifestations). The second spot as employed in the present invention is coated with sterilized normal animal serum. The dyes are selected, such that, when the carrier particles to which the dyes are bound are suspended, as when a liquid test specimen is added, a third color is formed, e.g., through a color additive or color substractive process, and which is clearly distinguishable from the color of each dye used in connection with the first and second reagent spots. For example, when a specimen of body fluid is placed in the well of the test device having blue and yellow reagent spots and agitated, there is initially and immediately formed a suspension of the dyed carrier particles comprising the blue and yellow reagent spots. Due to the size of the substrate particles and the homogeneous and intimate character of the suspension, the suspension appears to the normal human eye to be green, a color clearly distinguishable from each of the blue and yellow reagent spots.

Thus, if the antigenic material being tested for is absent from the specimen, the third color (e.g., green) in the suspension persists. However, if the test is positive, that is, if the specimen contains the specific antigenic material which is the complementary substance in the determinant antigen-antibody pair, an agglutination reaction occurs within a relatively short period of time. As a result, the colored suspension formed by the combination of dyed substrate particles from the first and second reagent spot dissipates and a spot or deposit of agglutinated material having the color of the first reagent spot (e.g., blue) forms in the lower portion of the well. The dyed substrate particles which originate from the second reagent spot remain in suspension giving the liquid the color of the second spot. It should be understood that the present invention contemplates the use of a single spot which is formed using the separately dyed reagents. For example, a single green spot may be formed of admixed blue and yellow particles and subjected to the fluid specimen. Color separation will occur if the agglutination reaction takes place.

Thus, depending on the antigenic material being analyzed for, the selection of substrate particles and dyes, and the need for a reference standard, the instant invention can readily be used by one having minimal skill or training in a clinic, hospital or physician's office. However, for many of the tests for which the present invention is contemplated, in view of the simplicity of the method and limited number of steps to be performed testing may readily be performed in the home by one lacking technical skills.

As stated above, the present invention may be used in any immunochemical test for an antigenic material for which an antibody or antibody-like material may be obtained for use in conjunction with the aforementioned first reagent spot. This would include not only diagnostic or qualitative tests but also quantitative tests as well. In application of the present invention to the latter, the use of blanks, reference standards or fixed amounts of antibody to determine minimal amounts of antigenic material are techniques which may be employed.

With these and other objects, advantages and features of the invention that may become hereinafter apparent, the nature of the invention may be more clearly understood by reference to the following detailed description of the invention, the appended claims and to the several drawings attached herein.

DESCRIPTION OF THE PREFERRED EMBODIMENTS

Figure 1:
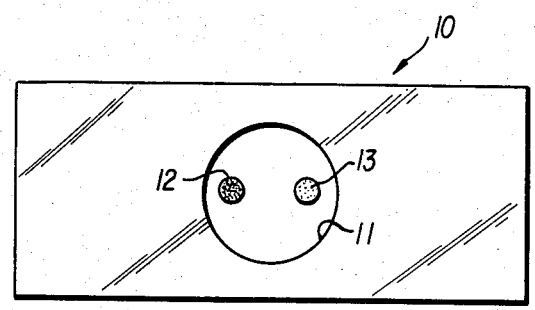
FIG. 1 is a plan view of a first embodiment of the present invention, a test slide with the reagent spots placed thereon.

Referring now to the drawings, FIG. 1 shows a test slide 10 having a well or indentation 11 therein. The well ranges in diameter from about 1 to 2.5 cm, preferably from about 1.5 to 2 cm in diameter, and has a depth of from about 1 to 10 mm, preferably about 2 to 6 mm. Suitable materials for the slide 10 include glass, plastic and cardboard. When the latter material is used, it is preferable that at least the surface of the well be coated with some liquid impervious and inert material such as wax or a polymeric material.

Figure 1A:
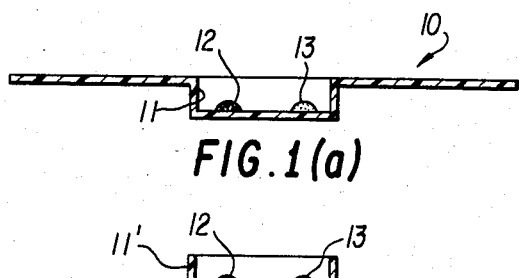
FIG. 1(a) is a partial sectional view taken along the line I—I of FIG. 1.
Figure 1B:
FIG. 1(b) is a variation of the embodiment shown in FIG. 1 and 1(a), in partial section.

A small reagent spot 12 consisting of dye-bound substrate with an antibody coating thereon is placed in close proximity to a second reagent spot 13, both of which are placed in a lower portion of the well. Reagent spot 13 is a dye bound substrate with a coating of normal animal serum. The dyes used in each reagent spot are different from each other. Although an indentation 11 as shown in FIG. 1(a) is preferred to receive the spots 12, 13, it is not essential to the present invention. Thus, for example as shown in FIG. 1(b), slide 10 can be formed with upstanding wall member 11' which surrounds spots 12, 13 forming an enclosure for receiving a liquid specimen therein.

Figure 4:
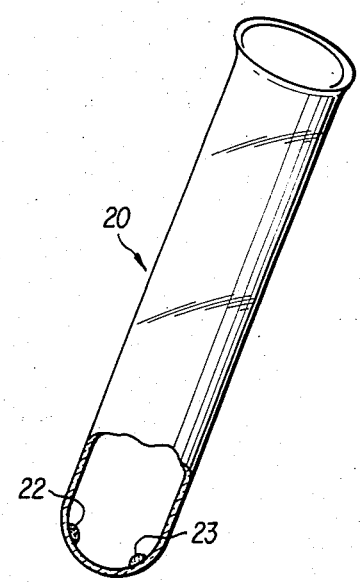
FIG. 4 is a perspective view of another embodiment of the present invention, with the reagent spots placed therein.
Figure 5:
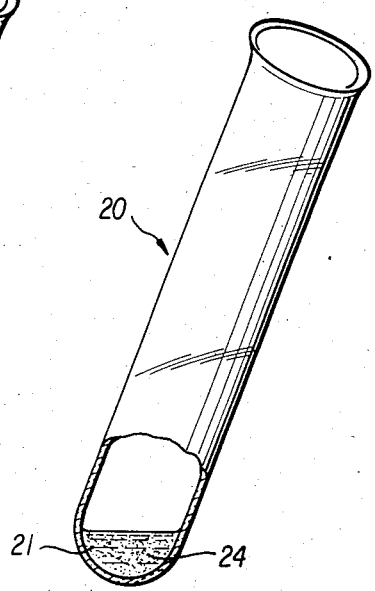
FIG. 5 is a perspective view of the test tube of FIG. 4 showing the admixed reagent spots immediately after adding a test specimen.
Figure 6:
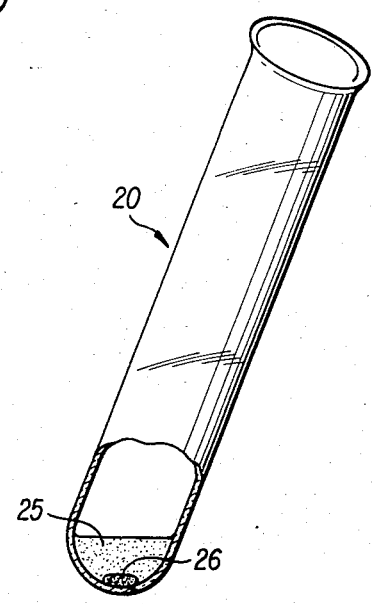
FIG. 6 is a perspective view of the test tube of FIG. 4 showing a positive test.

FIGS. 4 to 6 show a second embodiment of the present invention in which two reagent spots 22 and 23 are placed at the bottom of a closed-ended tube 20 in the well portion 21. In this embodiment, a test tube, vial or cuvette, made of a suitable material such as glass or plastic, may be employed.

Although the test devices disclosed herein may be prepared at the time of their use, it is contemplated that they will find their greatest utility as pre-prepared and pre-packaged test kits to be used in clinics, hospitals, physicians offices or in the home.

The test utensils of the present invention are prepared by placing reagent spots in the circumscribed test area by metering a predetermined volume of reagent suspension of predetermined concentration. The spots may then be dried by standard evaporative techniques such as air, air blast, vacuum drying or lyophilization. It is also contemplated that the reagent spots may be applied in the form of concentric rings or placed in superposed relation. What is important in the use of two differently colored reagents which when mixed yields another color. Color separation occurs upon agglutination when the direct agglutination test is used. The test utensils are then suitably packaged to seal them from biological and chemical contaminants as well as moisture. Such a packaged kit can be used not only for diagnostic or qualitative types of analyses but also in those situations in which quantitative measurements are being made. Such situations would include determination of above or below normal concentrations of anti-genic material due to an abnormal or pathological condition in the body of the subject. In such situations comparison may be made to a standard of known concentration. Alternatively, the kit can be prepared with a series of tubes or test slides having varying predetermined amounts of reagent spots on each device in the series.

Substrate materials which are suitable carriers for the dyes and antibodies, antiserum or animal serums of the present invention, include well known microparticles of suitable organic and inorganic materials, including lattices of organic polymers; bacteria such as *Staphylococcus aureus;* inorganic oxides such as silca, alumina; ethrocytes, bentonite, collodium, and cholesterol crystals. Suitable lattices of organic polymers innlude polystyrene, butadiene, copolymerized styrene-butadiene, acrylic or mixtures thereof. The particle size range of the latex substrate would suitably, but not exclusively, be from about 0.1 to less than about 5.0 microns, with the preferred range being from about 0.25 to about 1.5 microns and the most preferred being from about 0.35 to about 1.25 microns. The bacteria size typically ranges from about 1 to 3 microns, and is most preferred.

Figure 2:
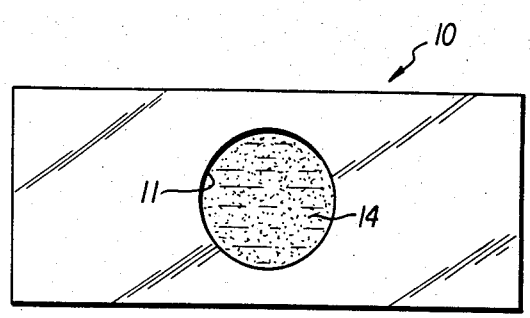
FIG. 2 is a plan view of a test slide of FIG. 1 showing the admixed reagent spots immediately after addition of a test specimen.
Figure 3:
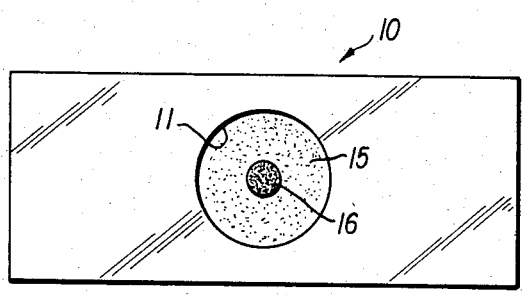
FIG. 3 is a plan view of a test slide of FIG. 1 showing a positive test.

The choice of dyes to be selected is determined by a number of factors. Most important to the effectiveness of the test is that the normal human eye be able to differentiate between the colors of the individual test spots, since these colors reappear in the instance of a positive test in the form of one or more spots of the agglutinated material formed from the antibody- or antiserum-sensitized substrate and the anti-genic material. However, it is also necessary that the normal human eye be able to distinguish between the color resulting from physical intermixing of the suspended dye-bound substrate particles when the specimen being tested is added to the test utensil, that is, the physically combined substrate particles from both reagent spots, and the colors of the individual dye-bound substrate particles of each of the reagent spots. Any color-detecting system which permits such visual distinctions is suitable. A color additive system has been successfully used in the present invention. One preferred example of the color additive system employs a blue dye for one reagent substrate and a yellow dye for the other reagent substrate. Thus, when the solution being tested is added to the test utensil and briefly agitated, the blue and yellow dyed substrate particles become intermixed and a uniform green color is formed. As shown in FIGS. 2 and 5 of the drawing, a uniformly colored suspension 14 and 24, respectively, is formed shortly after agitation of the added test specimen. If there is antigenic material present in the specimen sample which is specific to the antibody or antiserum present on one of the dyed substrates, agglutination occurs and a visually detectable blue or yellow spot or spots will appear in the receptacle depending on which of the dyed substrates is used as the antibody carrier. As shown in FIGS. 3 and 6, the agglutinated spots 16 and 26, correspond to the original antibody coated reagent spots 12 and 22, respectively, and the colored background 15 and 25, corresponding to original animal serum carrier spots 13 and 23, respectively. Thus, in the embodiments shown, spots 12 and 22 are formed of blue dyed antibody carrier particles and spots 13 and 23 are formed of yellow dyed animal serum carrier particles. A positive test yields a blue center spot 16, 26 as shown in FIGS. 3 and 6, respectively, surrounded by a yellow liquid 15, 25.

Other factors which enter into the selection of a suitable dye are the affinity of the dye for the substrate, inertness or lack of reactivity of the dye and permanence under the conditions it is being used. With the foregoing in mind, suitable dyes include those colored compounds which bind or can be attached to components or functional groups on nucleic acids carbohydrates, proteins, peptidoglycans, or lipids.

The concentration of the dyes, weight of dye and substrate may be varied. Sufficient dye should be used to impart the required color intensity. In practice the carrier particles may be dyed by conventional methods such as those set forth in U.S. Pat. No. 3,088,875, 3,236,732 and 4,166,105. Generally, after dyeing, the carrier particles are coated or sensitized with a solution, including suitable buffers, of the appropriate antibody, antiserum or normal animal serum, also by recognized precedures, such as those described in U.S. Pat. Nos. 3,088,875, 3,236,732, 3,234,096 and 3,309,275.

The concentrations (by weight) of the antibody or antiserum and normal animal serum to the total weight of the coated dye particles on a dry basis generally but not exclusively range between 0.005 and 5.0%, and preferably between about 0.01 and 1.0%. Potentiating agents such as glutaraldehyde are also useful in increasing the agglutination effect. Such agents are described in U.S. Pat. No. 4,088,749.

Suitable for use as the normal animal serum are such sterilized serums which are in standard use in immunological procedures. Normal goat serum and normal rabbit serum being preferred.

The present invention also contemplates the use of sandwich type coated or sensitized particles in which the dyed particles are precoated with a protein which is inert to any of the substances encountered during the subsequent coating with antibodies (antiserums) or during the diagnostic test itself. These types of particles and a method for their preparation are described in U.S. Pat. No. 3,551,555.

It is expected that the present invention will find major, though not exclusive, application in the detection of the presence of HCG, such as the diagnosis of pregnancy. The carrie particles employed and one method for preparing such particles are described in U.S. Pat. No. 3,551,555. The following example is intended to illustrate the principles of the present invention as applied to a pregnancy test. However, it is to be understood that the instant invention is in no way limited to such application but extends to a wide range of immunological analyses, as aforementioned.

EXAMPLE

The initial reagent spots 12, 13 are formed using heat inactivated bacteria, formalin-fixed protein A containing Staphylococcus aureus having a particle size of approximately 1.0 microns. The bacteria particles which ultimately form the agglutinating agent are dyed blue with Acid Blue 15 (C.I. No. 42645). The bacteria particles which carry the normal animal serum are dyed yellow using Auramine 0 (C.I. No. 41000). The blue dyed particles are sensitized with the IgG fraction of a rabbit anti-HCG serum. This material may be produced according to standard techniques or may be purchased from commercial producers. Normal rabbit serum which may also be produced according to conventional methods is used to coat the yellow dyed bacteria particles.

The test is performed by adding several drops of conventionally filtered urine specimen to the receiving portion of the test device 10 or 20 containing the spots. If the device 10 illustrated in FIG. 1 is employed, an inert and sterile stirring, rod is used to agitate the specimen; whereas, if the tube-type device 20 illustrated in FIG. 4 is employed, agitation is accomplished by covering the open end of the tube with a cap and swirling.

Shortly after agitation of the test solution a green suspension is formed. If HCG is present in the test specimen, agglutination will occur and within ten minutes a positive test is indicated by the formation of one or more spots of blue 16,26 in the midst of a yellow background 15, 25. It is this distinctive color change which is readily detectable by one having no technical skills which provides a marked advantage over known test procedures.

Although only a preferred embodiment is specifically illustrated and described herein, it will be appreciated that many modifications and variations of the present invention are possible in light of the above teachings and within the purview of the appended claim without departing from the spirit and intended scope of the invention.

What is claimed is:

1. A diagnostic device for detecting an antigenic material by visual color change resulting from antigenic-antibody reaction comprising:
   a first reagent spot carried by a substrate and dyed to form a first color;
   a second reagent spot carried by a substrate and dyed to form a second color which is visually distinct from said first reagent;
   means for mixing said dyed reagent spots and a fluid specimen for for forming a a suspension having a color which is visually different than the colors of said first and second dyed reagents.

2. The diagnostic device of claim 1 wherein one of said reagents comprises an antibody carried by a substrate, said substrate selected from the group consisting of organic and inorganic agglutimalle particles.

3. The diagnostic device of claim 1 wherein said substrate is a latex polymer or copolymer selected from the group consisting of styrene, butadiene, acrylic latex and mixtures thereof.

4. The diagnostic device of claim 2, wherein at least one of said substrates is particles of bacterial material.

5. The diagnostic device of claim 2, wherein said first dye absorbs light in a first part of the spectrum, said second dye absorbs light in a second part of the spectrum and a physical combination of said first dye and said second dye appears to absorb light in a third portion of the spectrum and each dye is distinguishable by the human eye.

6. The diagnostic device of claim 1, wherein said mixing means comprises a test slide.

7. The diagnostic device of claim 1, wherein said mixing means comprises a tube sealed at one end.

8. The diagnostic device of claims 2, wherein said antibody is selected from the group consisting of anti-hormones, anti-drugs, anti-rheumatoid factor, anti-blood plasma proteins, anti-bacterials, and anti-virals.

9. The diagnostic device of claim 3, wherein said antibody is anti-HCG.

10. The diagnostic device of claim 8, wherein said bacteria are heat inactivated, formalin fixed, protein A containing Staphylococcus aureus bacteria.

11. The diagnostic device of claim 4, wherein said bacteria particles are within the size range of about 0.50 to 3.0 microns.

12. The diagnostic device of claims 2, wherein said second reagent comprises bacteria particles which carry normal animal serum.

13. The diagnostic device of claim 12, wherein said normal animal serum is normal rabbit serum.

14. The diagnostic device of claim 2, wherein said first dye and second dye are each independently selected from the groups of colored compounds which bind or can be bound to components of nucleic acids, carbohydrates, proteins, peptiloglycans, or of lipids.

15. The diagnostic device of claim 2, wherein said first dye appears blue to the normal human eye and said second dye appears yellow to the normal human eye.

16. The diagnostic device of claim 2, wherein each of said substrate particles comprise protein A containing bacteria having particle sizes ranging from about 0.50 to 3.0 microns, said antibody is anti-HCG, said second substrate carries normal animal serum, one of said first reagents is blue, said other reagent spot is yellow, said blue and yellow colored particles forming a green color when admixed.

17. The diagnostic device of claim 16, wherein each of said reagents is separately formed in said mixing means in spaced relationship.

18. The diagnostic device of claim 16, wherein said Straphylococcus aureus bacteria are stained, heat killed and formalin treated.

19. A serological method of detecting the presence of an antigenic material in a body fluid of an animal host comprising:
(a) adding a specimen of said body fluid to a device for detecting said antigenic material, said test device including a test receptacle, a pair of reagent spots formed of particulate material of an organic or inorganic nature, each of said reagent spots having a dye which differs visually from the other such that when admixed a third color is observed;
(b) moving said fluid specimen in contact with said reagent spots to suspend said reagents therein;
(c) permitting said reagents to react and observing any color change due to the presence of antigenic material in said specimen, said color change resulting from an antigen-antibody reaction which causes separation of said admixed colors.

20. The serological method of claim 19, wherein said animal host is human and one of said reagents is a substrate carrying an antibody.

21. The serological method of claim 19, wherein said body fluid is selected from the group consisting of urine, blood, plasma, serum, saliva, and cerebrospinal fluid.

22. The serological method of claim 19, wherein said body fluid is urine.

23. The serological method of claims 19, wherein at least one of said substrates comprises particles of latex.

24. The serological method of claim 19, wherein said first dye absorbs light in a first part of the spectrum, said second dye absorbs light in a second part of the spectrum and a physical, combination of said first dye and said second dye appears to absorb light in a third portion of the spectrum.

25. The serological method of claim 19, wherein said first dye and said second dye absorb light in parts of the visual spectrum, distinguishable as different colors by the normal human eye.

26. The serological method of claim 19, wherein said test is performed on a test plate wherein said reagent spots are placed thereon.

27. The serological method of claim 19, wherein said test is performed using a test tube, the bottom portion for receiving said reagent spots.

28. The serological method of claim 26 wherein said spots are placed in an indentation or well.

29. The serological method of claim 20, wherein said antibody is selected from the group consisting of anti-hormones, anti-drugs, anti-rheumatoid factor, anti-blood plasma proteins, anti-bacterials, and anti-virals.

30. The serological method of claim 20, wherein said antibody is anti-HCG.

31. The serological method of claim 23, wherein said particles are selected from the group consisting of polystyrene latex, butadiene latex, copolymerized styrene-butadiene latex and acrylic latex.

32. The serological method of claim 23, wherein said latex particles bound to said first dye having particle sizes within the range of about 0.1 to 5.0 microns.

33. The serological method of claim 23, wherein said latex particles bound to said second dye having particle sizes within the range of from about 0.35 to 1.25 microns.

34. The serological method of claim 19, wherein said second reagent spot is coated with normal animal serum.

35. The serological method of claim 19, wherein said first dye and said second dye stain components on nucleic acids, carbohydrates, proteins, peptidoglycans, or lipids with the proviso that said first dye is different from said second dye.

36. The serological method of claim 19, wherein said first dye appears blue to the normal human eye and said second dye appears yellow to the normal human eye.

37. The serological method of claim 23, wherein each of said substrate particles comprise polystyrene latex particles having particle sizes ranging from about 0.35 to 1.25 microns, said antibody is anti-HCG, said normal animal serum is normal rabbit serum, one of said spots is blue, the other spot is yellow.

38. The serological method of claim 20, wherein one of said substrates is coated with *Staphylococcus aureus* bacteria.

39. The serological method of claim 38, wherein said *Straphylococcus aureus* bacteria is stained, heat killed and formalin treated.

40. In a direct agglutination pregnancy test which employs particles coated with antibodies for reacting with HCG found in the fluid specimen taken from the person suspected of being pregnant, the improvement comprising the steps of: providing a pair of reagent spots, each being colored differently, one of said spots containing said antibody, admiting said spots to form a color which differs visually from the colors associated with each of said reagent spots, permitting the agglutination reaction to proceed by contacting said clinical specimen with said reagents and, observing agglutination by the reformation of the color associated with said reagent spot carrying said antibody to HCG.

41. The direct agglutination pregnancy test according to claim 40, wherein the particles are selected from the group consisting of latex and *Straphylococcus aureus* bacteria.

42. The direct agglutination pregnancy test according to claim 41 wherein one of said reagent spots is colored blue, the other reagent spot being colored yellow and when admixed the resulting color is green.

43. The direct agglutination pregnancy test according to claim 41 wherein the reagent spot carrying the anti-HCG is colored blue and the second reagent spot is colored yellow.

44. The direct agglutination pregnancy test according to claim 43 wherein the second reagent spot is formed of normal animal serum.

45. A kit for detecting pregnancy using an immunological color change test comprising:
 a. test receptacle for receiving a fluid specimen;
 b. a pair of reagent spots positioned on said test receptacle, each of the reagent spots being provided with a color which is visually distinct from one another, one of said colored reagent spots carrying antibodies for HCG;
 c. said test receptacle being constructed to receive said fluid specimen in direct contact with said reagent spots whereby said spots are admixed to form another color which is readily discernible from either of the initially formed spots.

46. The kit of claim 45 wherein the reagent spots are spaced apart.

* * * * *